United States Patent
Hodges

(10) Patent No.: US 10,029,038 B2
(45) Date of Patent: Jul. 24, 2018

(54) CANTILEVERED ROTOR PUMP AND METHODS FOR AXIAL FLOW BLOOD PUMPING

(71) Applicant: Thoratec Corporation, Pleasanton, CA (US)

(72) Inventor: William V. Hodges, Tracy, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 15/216,528

(22) Filed: Jul. 21, 2016

(65) Prior Publication Data

US 2017/0021069 A1    Jan. 26, 2017

Related U.S. Application Data

(60) Provisional application No. 62/195,258, filed on Jul. 21, 2015.

(51) Int. Cl.
*A61M 1/12* (2006.01)
*A61M 1/10* (2006.01)

(52) U.S. Cl.
CPC ........ *A61M 1/1013* (2014.02); *A61M 1/1036* (2014.02); *A61M 1/101* (2013.01); *A61M 1/1012* (2014.02); *A61M 1/1025* (2014.02); *A61M 1/1031* (2014.02); *A61M 1/122* (2014.02)

(58) Field of Classification Search
None
See application file for complete search history.

(56) References Cited

U.S. PATENT DOCUMENTS

| | | | |
|---|---|---|---|
| 2,712,792 A * | 7/1955 | Snyder | A61M 1/00 418/154 |
| 5,376,114 A * | 12/1994 | Jarvik | A61M 1/102 128/898 |
| 5,405,251 A * | 4/1995 | Sipin | F04D 13/0666 415/146 |
| 5,588,812 A | 12/1996 | Taylor et al. | |
| 5,695,471 A | 12/1997 | Wampler | |
| 5,888,242 A | 3/1999 | Antaki et al. | |
| 5,928,131 A * | 7/1999 | Prem | F04D 13/0646 310/90.5 |
| 5,947,892 A * | 9/1999 | Benkowski | A61M 1/10 415/900 |
| 5,957,672 A * | 9/1999 | Aber | A61M 1/10 384/907.1 |
| 6,071,093 A | 6/2000 | Hart | |
| 6,116,862 A | 9/2000 | Rau et al. | |

(Continued)

*Primary Examiner* — Kennedy Schaetzle
(74) *Attorney, Agent, or Firm* — Kilpatrick, Townsend & Stockton LLP

(57) ABSTRACT

Blood pump devices having improved rotor design are provided herein. Such blood pump devices include rotors having cantilevered support through a sealed mechanical bearing disposed outside a blood flow path of the device so as to avoid thrombus formation caused by blood contact with the bearing. The bearing means can be rotatably coupled with a proximal portion of the rotor shaft extending outside the fluid path, while a stator drives rotation of the rotor shaft so that one or more rotor blades on a distal portion of the rotor force blood flow through the device. The bearing means may include one or more radial bearings on a proximal portion of the rotor shaft that are isolated from the blood flow path by one or more rotary seals.

9 Claims, 7 Drawing Sheets

(56) References Cited

U.S. PATENT DOCUMENTS

| | | | |
|---|---|---|---|
| 6,135,710 A * | 10/2000 | Araki | A61M 1/1036 415/206 |
| 6,186,665 B1 | 2/2001 | Maher et al. | |
| 6,227,820 B1 | 5/2001 | Jarvik | |
| 6,234,772 B1 | 5/2001 | Wampler et al. | |
| 6,254,359 B1 | 7/2001 | Aber et al. | |
| 6,264,635 B1 | 7/2001 | Wampler et al. | |
| 6,688,861 B2 | 2/2004 | Wampler | |
| 6,942,611 B2 | 9/2005 | Siess et al. | |
| 6,991,595 B2 | 1/2006 | Burke et al. | |
| 7,011,620 B1 | 3/2006 | Siess | |
| 7,699,586 B2 | 4/2010 | LaRose et al. | |
| 7,976,271 B2 | 7/2011 | LaRose et al. | |
| 7,997,854 B2 | 8/2011 | LaRose et al. | |
| 8,007,254 B2 | 8/2011 | Marquis et al. | |
| 8,152,493 B2 | 4/2012 | Tyagarajan et al. | |
| 8,323,174 B2 | 12/2012 | Jeevanandam et al. | |
| 8,449,444 B2 | 5/2013 | Poirier et al. | |
| 8,506,471 B2 | 8/2013 | Bourque | |
| 8,562,508 B2 | 10/2013 | Dague et al. | |
| 8,597,350 B2 | 12/2013 | Rudser et al. | |
| 8,652,024 B1 | 2/2014 | Yanai et al. | |
| 8,657,733 B2 | 2/2014 | Ayre et al. | |
| 8,668,473 B2 | 3/2014 | Marquis et al. | |
| 9,265,870 B2 | 2/2016 | Reichenbach et al. | |
| 9,533,082 B2 | 1/2017 | Reichenbach et al. | |
| 9,717,832 B2 | 8/2017 | Taskin et al. | |
| 9,717,833 B2 * | 8/2017 | McBride | A61M 1/122 |
| 2003/0068227 A1 * | 4/2003 | Yamazaki | A61L 31/022 415/200 |
| 2003/0135086 A1 * | 7/2003 | Khaw | A61M 1/1024 600/16 |
| 2005/0071001 A1 | 3/2005 | Jarvik | |
| 2007/0078293 A1 | 4/2007 | Shambaugh et al. | |
| 2008/0021394 A1 | 1/2008 | LaRose et al. | |
| 2009/0118567 A1 | 5/2009 | Siess | |
| 2009/0203957 A1 | 8/2009 | LaRose et al. | |
| 2012/0046514 A1 | 2/2012 | Bourque | |
| 2012/0095281 A1 | 4/2012 | Reichenbach et al. | |
| 2012/0172655 A1 * | 7/2012 | Campbell | A61M 25/04 600/16 |
| 2013/0096364 A1 | 4/2013 | Reichenbach et al. | |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0225909 A1 | 8/2013 | Dormanen et al. | |
| 2013/0314047 A1 | 11/2013 | Eagle et al. | |
| 2014/0324165 A1 | 10/2014 | Burke | |
| 2015/0285258 A1 * | 10/2015 | Foster | A61M 1/12 415/203 |
| 2016/0144089 A1 | 5/2016 | Woo et al. | |
| 2016/0369814 A1 * | 12/2016 | Schibli | F04D 3/00 |

* cited by examiner

CANTILEVERED ROTOR PUMP AND METHODS FOR AXIAL FLOW BLOOD PUMPING

CROSS-REFERENCES TO RELATED APPLICATIONS

This application claims the benefit of U.S. Provisional Application No. 62/195,258, filed on Jul. 21, 2015, and entitled "CANTILEVERED ROTOR PUMP AND METHODS FOR AXIAL FLOW BLOOD PUMPING," the entirety of which is hereby incorporated herein by reference.

This application relates generally to U.S. application Ser. No. 14/489,041 entitled "Pump and Method for Mixed Flow Blood Pumping" filed Sep. 17, 2014; U.S. application Ser. No. 13/273,185 entitled "Pumping Blood" filed Oct. 13, 2011; each of which is incorporated herein by reference in its entirety for all purposes.

BACKGROUND

This application relates generally to mechanical circulatory support systems, and more specifically relates to improved rotor designs in axial flow blood pumps.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

While blood pumps have been effective for many patients, because patients using such devices are living longer, further improvements that prolong the effectiveness and lifetime of such blood pump devices are desired. One challenge frequently encountered in axial blood pumps is the development of thrombus in the bearing assemblies supporting the rotor. Thus, there is a need for improved blood pump designs that avoid thrombus formation over the lifetime of the device.

BRIEF SUMMARY

An axial flow mechanical circulatory support system having an improved rotor design with resistance to thrombus formation is provided herein.

In one aspect, blood pumps having improved rotor designs that are supported by mechanical bearings that avoid contact with blood are described herein. In some embodiments, such improved blood pumps include: a pump housing defining a blood flow passage; a rotor including a rotatable shaft and one or more rotor blades extending laterally from the rotatable shaft within the blood flow path to facilitate flow of blood upon rotation of the rotor; and a rotation means adapted for driving rotation of the rotatable shaft. Advantageously, the rotor can be rotatably coupled to the housing through a sealed mechanical bearing that remains outside the blood flow path such that blood contact with the bearing is avoided, thereby avoiding formation of thrombus on the bearing assembly and avoiding the need for washing or flushing the bearing with blood fluid or saline fluid. Typically, the rotation means includes a stator motor and the rotatable shaft includes a number of magnetic elements driven by the stator. In some embodiments, the bearing assembly is rotatably coupled with the rotor shaft at or near the proximal end of the rotor shaft that extends outside of the blood flow path while a distal portion of the rotor shaft remains within the blood flow path and free from attachment to the pump housing such that the mechanical bearing provides cantilevered support of the rotor during operation.

In one aspect, the bearing assembly is rotatably coupled with the rotor shaft along a proximal portion of the rotor shaft axially separated from a distal portion from which the one or more rotor blades extend. In some embodiments, the bearing assembly is axially separated from the one or more rotor blades by a separation distance, such as between 0.1 and 10 cm, or more preferably between 0.25 cm and 5 cm. In some embodiments, the rotor includes comprises a series of rotor blades that are distributed circumferentially about the rotor. The rotor blades, rotor and/or the rotor shaft may be formed of different materials or the same materials and may be assembled from separate parts or integrally formed.

In some embodiments, the rotor is disposed substantially or entirely within the pump housing during operation of the device. The rotor may be assembled by removal of a rear cover of the housing, the rear cover including a circular hole through which a proximal portion of the rotor shaft extends before attachment to the bearing assembly. In some embodiments, the mechanical bearing assembly resides within a cavity in the rear cover isolated from the blood flow path within the housing. One or more rotary seals may be used to fluidly-seal the mechanical bearing from any contact with blood.

In one aspect, the rotor shaft is substantially rigid and extends directly from the sealed bearing assembly to the rotor blades within the blood flow path defined by the pump housing. In some embodiments, the rotor is sufficiently rigid so as to inhibit lateral deflection of a distal portion of the rotor on which the one or more blades are disposed. The rotor can be selected of a material sufficiently rigid such that a maximum lateral deflection during operation of the blood pump is less than 0.1", less than 0.01" or less than 0.001". The rotor blades may also be substantially rigid, semi-rigid, flexible or a combination of rigid and flexible components. Typically, the rotor blades are rigid or semi-rigid and are disposed in a substantially fixed position and/or orientation relative the rotor shaft.

In another aspect, the sealed mechanical bearing assembly includes one or more radial bearings. The one or more radial bearings may be selected to have an axial thickness or width that extends along a longitudinal axis of the rotor. The radial bearing may be of a metallic (e.g. stainless steel) and/or a ceramic construction. The bearing assembly may include a lubricant, such as an oil-based or silicone lubricant, to facilitate movement of the radial bearings within the assembly. This aspect allows the bearing to withstand greater deflecting forces and/or to apply a greater reactive torque to the proximal portion of the rotor shaft so as to maintain a position and/or alignment of the rotor during operation. In some embodiments, the one or more radial bearings have a total axial width between 0.01" and 1", or more preferably between 0.050" and 0.500". The length of the rotor may be between 0.250" to 3.500". In some embodiments, the pump housing is substantially rigid and the rotor blades are disposed entirely within the blood flow path defined within the pump housing. In some embodiments, the rotor is driven by a drive shaft. The mechanical bearing may be incorporated into a rear cover that interfaces with the pump housing and may also be of rigid construction. In some embodiments, the drive shaft is substantially rigid and may be entirely internal to the blood pump, such that the shaft is driven without any need for motors or cables external to the blood pump to drive the rotor. In some embodiments, the rotor extends directly from the mechanical bearing to the rotor blades within the blood pump.

While it is appreciated that rotors of various sizes may be used, this design may utilize rotors of larger sizes, including rotors having an outer diameter in excess of 9 mm to facilitate higher blood flow rates. In some embodiments, the blood pump is adapted to pump blood at a flow rate of greater than 3.5 L/min at normal physiological pressure. In some embodiments, the blood pump is adapted to pump greater than 4 L/min, 5 L/min, 6 L/min, 7 L/min, 8 L/min, 9 L/min or 10 L/min. In some embodiments, normal physiological pressure is 60 mm Hg, while in other embodiments, normal physiological pressure is 30 mm Hg. In some aspects, normal physiological pressure can be 10 to 30 mm Hg for the right ventricle and 10 to 100 mm Hg or greater for the right ventricle.

In some embodiments, such devices are configured with rotors dimensioned to provide a suitable blood flow rate to provide ventricular assist while rotational speeds of the rotor are within a range of about 1,000 to 10,000 rpm, such as within a range of about 1,000 to 5,000 rpm. In some examples, suitable blood flow rates are any blood flow rate up to 10 L/min, and are often within a range of blood flows such as between 1 L/min to 12 L/min, between 3 L/min to 10 L/min, and 4 L/min to 6 L/min. Such rotors can be controlled so as to provide constant flow rates or variable flow rates as needed. It is appreciated that such pump devices can be controlled so as to provide lower blood flow rates as needed, for example depending on the level of assist required by the blood flow pump.

In another aspect, the rotor is supported at a first end by a bearing assembly and includes one or more rotor blades at a second end opposite the first end that is unsupported such that the rotor is cantilever. In some embodiments, the first end is incorporated into an implanted device. In some embodiments, the rotor is supported only at the first end of the rotor.

In another aspect, such devices include one or more rotary seals disposed along the rotor shaft between the bearing assembly and the one or more rotor blades so as to fluidly seal the bearing assembly from any blood flowing through the blood flow path. In some embodiments, a blood pump includes a housing with an inner wall defining an inlet, an outlet downstream from the inlet, and a blood flow path between the inlet and the outlet. A rotor extending between a proximal and distal end, which extends distally into the blood flow path and includes magnetic material to facilitate being rotationally driven by a stator. A motor stator positioned about the blood flow path defined at least in part by the pump housing between the inlet and the outlet of the pump. The motor stator, during operation, is configured to generate a magnetic field for rotating the rotor to force blood along the blood flow path by rotation of one or more rotor blades along a distal portion of the rotor. A mechanical bearing assembly is disposed outside the blood flow path and rotatably couples a proximal portion of the rotor with the pump housing.

Methods of pumping blood in accordance with aspects of the invention are also provided. In some embodiments, such methods include operating a blood pump so as to transport blood along a blood flow path through a blood flow pump. Operating the blood pump may include rotating a rotor by use of a stator extending about the blood flow path so that movement of one or more rotor blades on a distal portion of the rotor forces blood along the blood flow path; and maintaining a position and/or alignment of the rotor during rotation by rotatably securing the rotor with a mechanical bearing disposed outside the blood flow path thereby inhibiting thrombus formation in the bearing. Some methods can further include sealing the mechanical bearing from the blood flow path with a radial seal extending about the rotor between the mechanical bearing and a distal portion of the rotor having the one or more rotor blades in contact with blood along the blood flow path. In some embodiments, alignment of the rotor within the blood flow path is maintained by resisting lateral applied forces from blood flow by applying a countering torque through the one or more radial bearings. Typically, the radial bearing is disposed at or near one end of the rotor such that the countering torque is cantilevered through the rotor.

In another aspect, the invention provides an implantable pump having a cantilevered rotor and a sealed bearing assembly. Such pumps can include a pump housing defining a flow passage therethrough and a cantilevered rotor having a rotatable shaft and extending at least partly within the flow passage to facilitate fluid flow through the passage upon rotation of the rotatable shaft. The rotor can include one or more rotor blades, fins, depression, or various other features as needed to facilitate fluid flow upon rotation of the shaft. The sealed bearing assembly supportingly couples the rotatable shaft within the pump and is sealed from contact with fluid flowing through the flow passage during operation of the pump. In some embodiments, the bearing assembly is disposed at or near one end of the rotor such that the rotatable shaft is cantilevered. The bearing assembly can be disposed outside the flow path defined by the pump housing. The bearing assembly typically includes lubricant sealed within. Since the bearing assembly is sealed from its environment, the bearing assembly can include one or more bearing components and/or lubricants that are non-biocompatible. The bearing assembly can also include sealed within one or more off-the-shelf shelf bearing components that are standard for non-implantable applications or various types of pumps. The mechanical bearing assembly can also be sealed without any fluid channel for flushing the bearing assembly.

In yet another aspect, such pumps can include a cantilevered rotor that extends along a first axis and a fluid flow path defined to direct fluid along the first axis and divert fluid flow along one or more other axes, such as a second axis that is transverse to the first axis. In some embodiments, the first and second axes are substantially perpendicular. Such pumps can be configured as a blood pump, the mechanical bearing assembly being sealed from blood flowing through the flow passage so as to inhibit thrombus formation by avoiding contact between the bearing assembly and any blood flowing through the flow passage. In such embodiments, the pump can be configured such that a flow inlet of the pump directs fluid from a ventricle of the heart along the first axis, during rotation of the cantilevered rotor, while the flow path diverts blood flow along a second axis that is transverse to the first axis to a flow outlet for delivery to the aorta.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim. The invention will be better understood upon reading the following description and examining the figures which accompany it.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
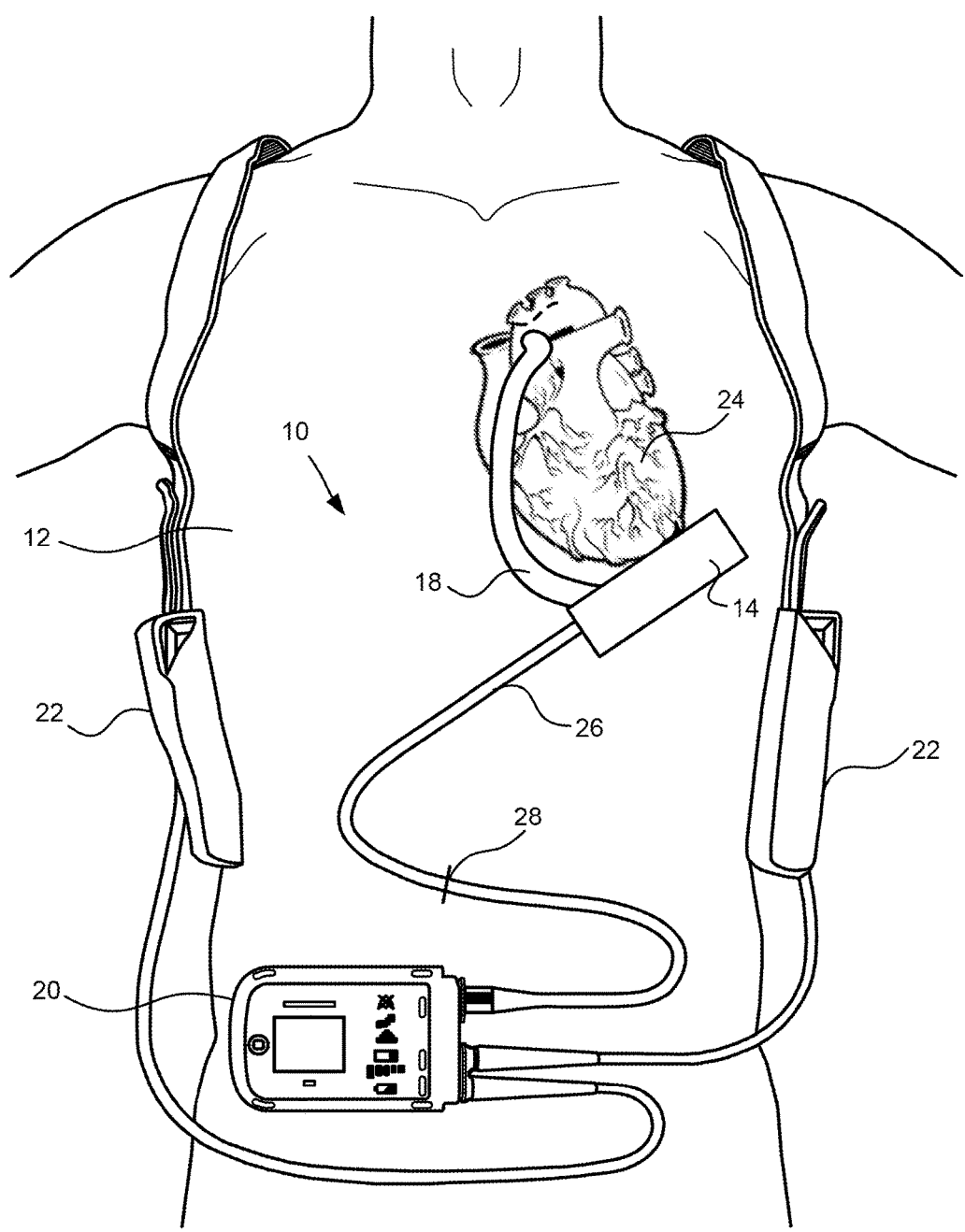
FIG. 1 is an illustration of a mechanical circulatory support system implanted in a patient's body in accordance with embodiments of the invention.

FIG. 1 is an illustration of a mechanical circulatory support system 10 implanted in a patient's body 12. The mechanical circulatory support system 10 comprises an implantable blood pump 14, outflow cannula 18, system controller 20, and power sources 22. The implantable blood pump 14 may comprise a VAD that is attached to an apex of the left ventricle, as illustrated, or the right ventricle, or both ventricles of the heart 24. The VAD is typically an axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. The blood pump 14 may be attached to the heart 24 via a ventricular cuff which is sewn to the heart 24 and coupled to the blood pump 14. The other end of the blood pump 14 connects to the ascending aorta via the outflow cannula 18 so that the VAD effectively diverts blood from the weakened ventricle and propels blood to the aorta for circulation to the rest of the patient's vascular system.

FIG. 1 illustrates the mechanical circulatory support system 10 during battery 22 powered operation. A driveline 26 which exits through an exit site 28 in the patient's abdomen, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump 14. Examples of such modifications are further described in U.S. Pat. No. 8,562,508 and U.S. Patent Publication No. 2013/0127253, each of which is incorporated herein by reference in its entirety for all purposes.

In some conventional blood pumps, the rotor is suspended by bearing assemblies near opposite ends of the rotor with the rotor blades between. The bearings are disposed within the blood flow path and lubricated, in part, by blood flowing across the bearings. Such bearings are known as blood-washed bearings.

Figure 2:
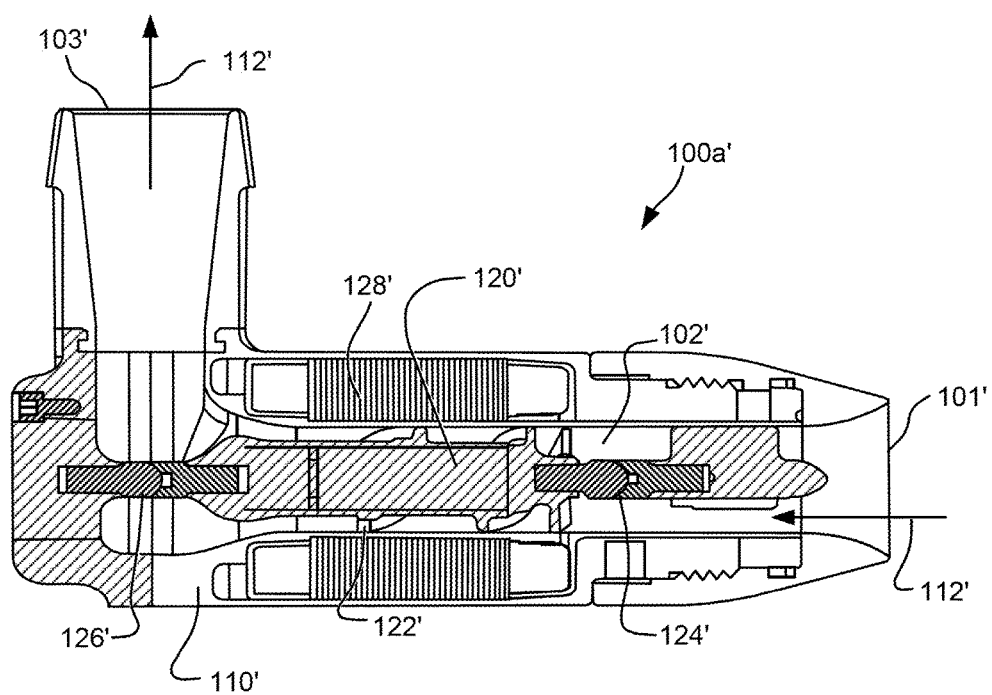
FIG. 2 shows a conventional axial blood flow pump device.

An example of such bearings can be understood by referring to FIG. 2, which shows a conventional axial flow blood pump 100'. The pump includes a housing 110' that defines a blood flow path 112'. Blood enters the housing 110' through an inlet 101', passes through a central tubular region 102' of the housing 110', and exits through an outlet 103'. The housing 110' contains a motor stator 128', which drives rotation of a rotor 120' located in the blood flow path 112'. As the rotor 120' rotates, blades 122' on the rotor 120' impart energy to the blood flow, resulting in pressure and blood flow at the outlet 103'. The rotor 120' is suspended in the housing 110' by fore and aft mechanical, blood-immersed bearings 124', 126' that limit axial translation of the rotor 120'. The bearings 124, 126 also limit the rotor from shifting off its axis of rotation and resist various destabilizing forces that occur during operation.

Studies have revealed that blood-washed bearings tend to develop thrombus over-time at the point of contact between the bearing ball and the cup in which the ball resides. Development of thrombus in the bearings can significantly degrade performance of the pump over time. In twelve chronic in-vivo animal studies, upon completion of the studies, the pumps were explanted and disassembled, after which it was observed that, in 50% of the pumps, either one or both bearings had some level of thrombosis evident.

To address these issues, recent developments include replacing blood washed mechanical bearings in rotary blood pumps that are used to suspend rotors with actively/passively magnetically suspended rotors. This allows for the removal of mechanical bearings in pumps, however, the magnetic levitation of the rotor creates hydrodynamic bearings between the pump housing and rotor. In addition, adding magnetics to VAD's significantly increases the complexity of the design and its operation since the magnets must generally maintain a radial position within the blood flow path as well as a longitudinal position. Due in part to these complexities, current versions of hydrodynamic bearings used in VAD's still frequently develop thrombus issues.

In one aspect, the invention addresses these challenges associated with conventional designs by reconfiguring the blood pump to include mechanical bearings that are excluded from the blood flow path. In some embodiments, the mechanical bearing is excluded from the blood flow path by use of a cantilevered rotor design in which the rotor is supported at one end by a mechanical bearing assembly that remains sealed outside of the blood flow path. In one aspect, the mechanical bearing assembly is sealed such that there is no need for washing the bearing with blood flow or flushing the assembly with saline. The mechanical bearing assembly can include one or more radial bearings at or near one end of the rotor, thereby providing cantilevered support during rotation of the rotor. In some aspects, the radial bearing can be of a metallic (e.g. stainless steel) or non-metallic (e.g. ceramic, polymer) construction. In one aspect, the design allows for the rotor to operate with a single fluid flow path for blood flow through the blood pump, without the need for additional fluid flow paths for saline flushing or waste return. In addition, by reconfiguring the design of the axial flow pump, the blood-washed mechanical ball and cup bearing design used in conventional axial pump designs can be eliminated. As a byproduct, the inlet stator, front bearing set, and rear bearing set can be removed from the design.

Figure 3:
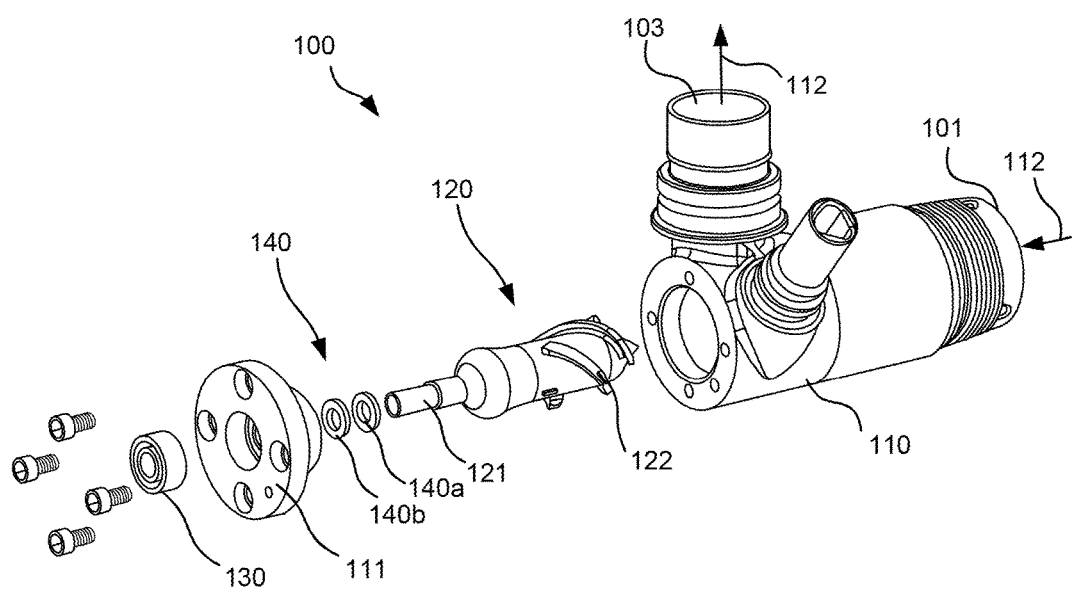
FIG. 3 shows an axial flow blood pump device with an improved rotor design in accordance with some embodiments.

FIG. 3 illustrates an exploded view of an embodiment of an axial blood flow pump design with an improved cantilevered rotor design. The improved axial flow blood pump 100 includes a housing 110 that defines a blood flow path 112 that enters the housing 110 through an inlet 101, passes through a central tubular region of the housing and exits through an outlet 103. Housing 110 may be non-magnetic and may be made of a biocompatible material such as titanium or a suitable ceramic material which is non-thrombogenic, rigid, and exhibits minimum eddy current losses. Housing 110 contains a rotating means, such as a motor stator, adapted to drive rotation of rotor 120. Rotor 120 includes one or more rotor blades 122, typically a group of helical blades, on a distal portion that extends into the blood flow path 112. As rotor 120 rotates, rotor blades 122 impart energy to the blood flow, resulting in pressure and blood flow at the outlet 103. Rotor 120 is suspended in the housing 110 by a mechanical bearing assembly 130 disposed on a proximal portion of rotor 120 that extends through a hole in the rear cover 11 outside the blood flow path.

In some embodiments, rotor 120 is redesigned such that a circular rotor shaft 121 that extends proximally from the rear of the rotor and outside the blood flow path. Such a configuration allows for use of a traditional mechanical bearing (not blood or saline washed). Mechanical bearing 130 can be assembled within the rear cover 111 of the pump housing 110 such that any contact with the blood flow stream is avoided. In this embodiment, the shaft of rotor 120 slides through back cover 111 and can be press fit into the bearing assembly. At the shaft to plug interface, a mechanical rotary seal can be used to further ensure blood contact is avoided. A design of this nature reduces the static to dynamic interfaces from two to one. Furthermore, unlike blood washed bearings, this design does not rely on blood as a lubricant. Rotary seal keeps the blood from being used as a lubricant, which allows blood to be eliminated as a lubricant within rotary type blood pump devices. Since a sealed mechanical bearing assembly is used, this allows for a bearing design that utilizes various other types of lubricant (e.g. oil-based, silicone) and could use and/or adapt common bearings and lubricants from the mechanical arts as would be understood by one of skill from the description herein. Such mechanical bearings may provide improved performance and durability and increased life-times as compared to saline purged or blood washed designs.

Since mechanical bearing 130 couples the rotor at only one end, it provides cantilevered support and withstands lateral deflection of the rotor by applying a torque through the proximal portion. In some embodiments, the mechanical bearing may be selected to have an axial thickness extending along an axis of the rotor shaft between 0.050" to 0.500" to allow the bearing to withstand greater deflecting forces and apply greater reactive torques. In some embodiments, the device may include a mechanical bearing 130 consisting of multiple stacked radial bearings, such as two stacked radial bearings, as shown in FIG. 4.

In another aspect, rotor 120 includes a fluid-tight seal 140 disposed between a proximal portion of the rotor coupled with mechanical bearing assembly 130 and a distal portion from which the rotor blades extend within the blood flow path. In some embodiments, such as that shown in FIG. 3, the rotary seal 140 comprises two interfacing components, first component 140a that is secured to the rotor shaft and revolves with the shaft and second component 140b that remains secured with rear cover 111. Typically, first component 140a is a flat component that engages against second component 140b, another component, so as to provide a fluid-tight seal and inhibit blood flow into the bearing assembly. One or both of the first and second components 140a, 140b can be formed of a hard and/or rigid material so as to withstand the variable forces that may occur during operation and maintain a fluid-tight seal over the lifetime of the device. Also, one or both of the seals may be attached and/or interface with a compliant member in order to provide seal preload and allow the seals to track on one another.

Figure 4:
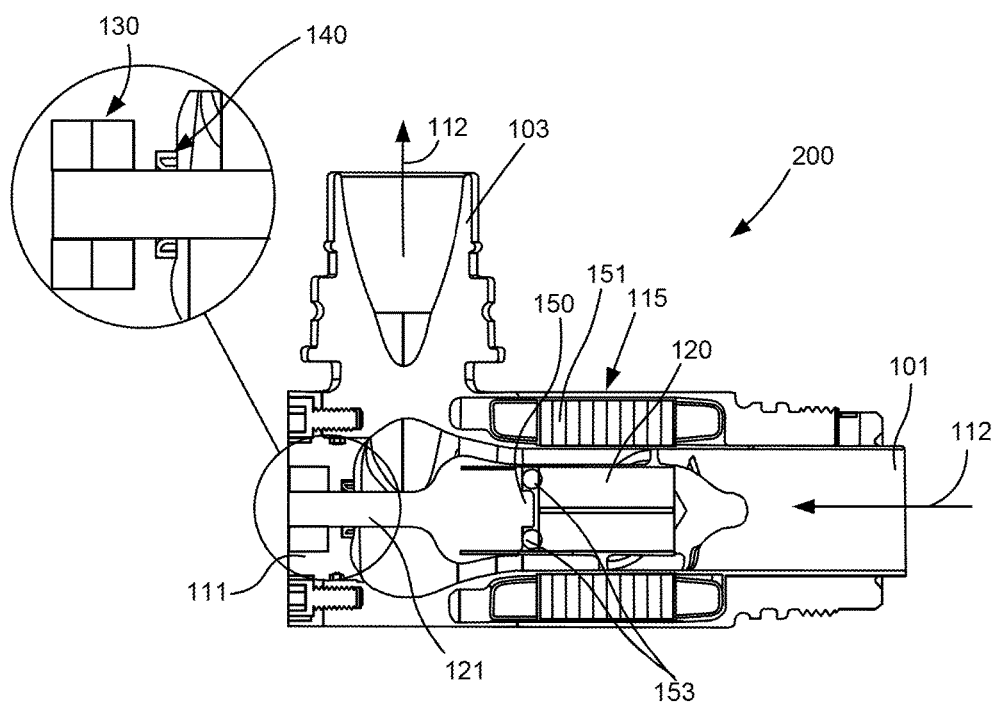
FIG. 4 shows another axial flow blood pump device with an improved rotor design in accordance with some embodiments.

FIG. 4 shows another exemplary pump 200 having a cantilevered rotor 120 in which the supporting mechanical bearing 130 is disposed outside the blood flow path. In this embodiment, mechanical bearing assembly 130 includes two radial bearings stacked on the proximal portion of the rotor 120. Rotor 120 includes permanent drive magnets 150 to facilitate being rotationally driven by a motor stator 151 having electrically conductive coils. The coils are placed within an enclosure which surrounds the blood flow path and the rotor 120 disposed within pump housing 110. The motor stator 151 serves to rotate rotor 120 by the conventional application of electric power to the coils to drive the permanent drive magnets 150 incorporated into rotor 120. Elastomeric O-rings 153 keep the magnets from rotating in the rotor. Such magnets are selected for magnetic properties, length, and cross-sectional area in order to provide good electromagnetic coupling with the magnetic forces created by the motor stator 151. In some embodiments, the motor is a three phase, brushless DC motor. In other embodiments, the motor can be a toroidal, three phase or wye connected design. The stator may have a back iron design which is consistent with a typical radial flux gap motor. If desired, motor stator 151 can be incorporated within a separate, hermetically sealed enclosure that slides over pump housing into position. In some embodiments, the body of rotor 120 includes a magnetically hard ferromagnetic material, i.e., a material which forms a strong permanent magnet and which is resistant to demagnetization. The material of rotor body 120 is typically selected to be biocompatible and substantially non-thrombogenic. Rotor 120 can be formed as a unitary component or can be formed of separate components joined together. In some embodiments, the rotor body is formed as a unitary mass of a suitable material, such as an alloy of platinum, titanium, and cobalt. In other embodiments, the rotor body may be formed from a magnetic metal such as an iron-nickel alloy with an exterior coating of another material to increase the body's biocompatibility. Further details regarding suitable rotor designs are described in U.S. Pat. No. 5,588,812; Ser. No. 62/084,946; 2016/0144089; 2014/0324165; and U.S. Pat. No. 9,265,870; each of which is incorporated herein by reference in its entirely for all purposes.

Figure 5:
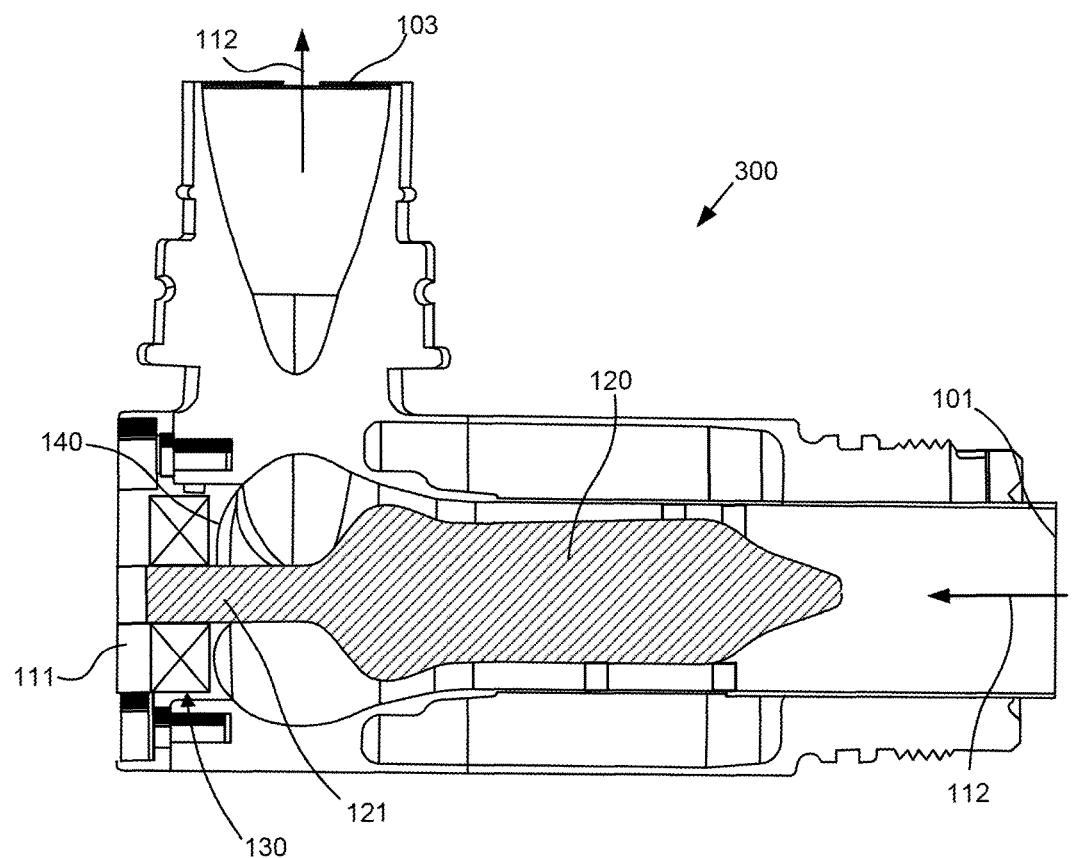
FIG. 5 shows another axial flow blood pump device with an improved rotor design in accordance with some embodiments.

FIG. 5 shows another exemplary axial pump device 300 having a cantilevered rotor 120 supported by a mechanical bearing 130. This embodiment includes a radial seal 140 that comprises a curved elastomeric seal that spans the interface between the rotor shaft 121 and the hole in the rear cover 111 through which the proximal portion of the rotor 120 extends. This configuration utilizes a flexible elastomeric seal to direct the flow of blood away from the interface and maintain a fluid-tight seal so as to isolate the mechanical bearing from any contact with blood, thereby avoiding formation of thrombus. In one aspect, since embodiments of the invention provide conditions that reduce blood coagulation and thrombus formation, a lower amount of anticoagulant may be used, which may result in fewer patient adverse side effects.

Figure 6:
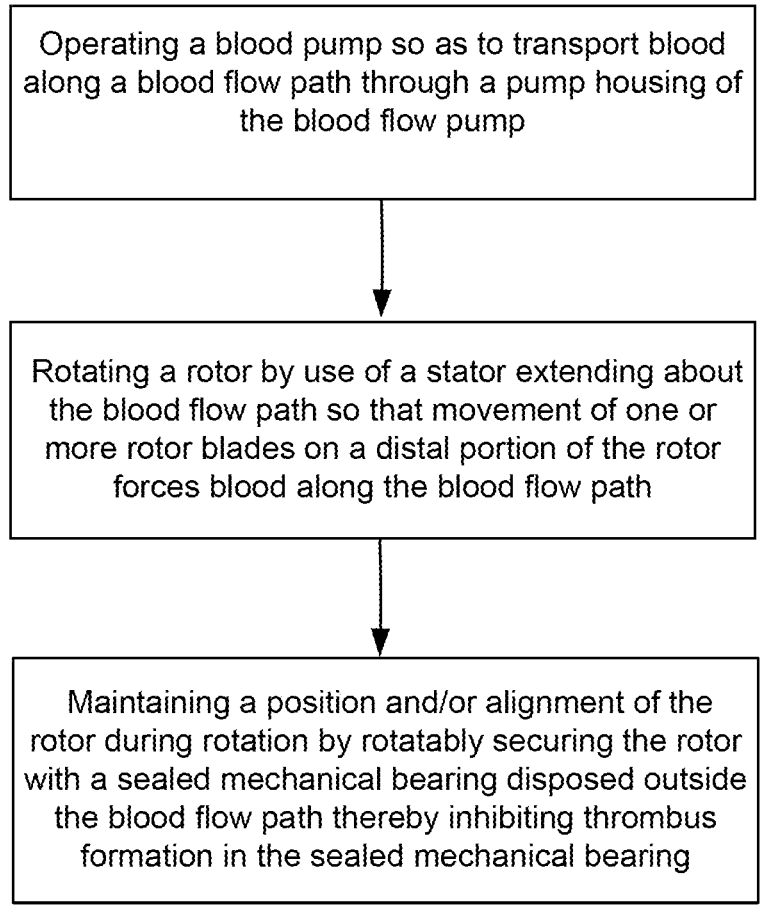
FIGS. 6-7 shows methods of pumping blood with a blood pump in accordance with some embodiments.
Figure 7:
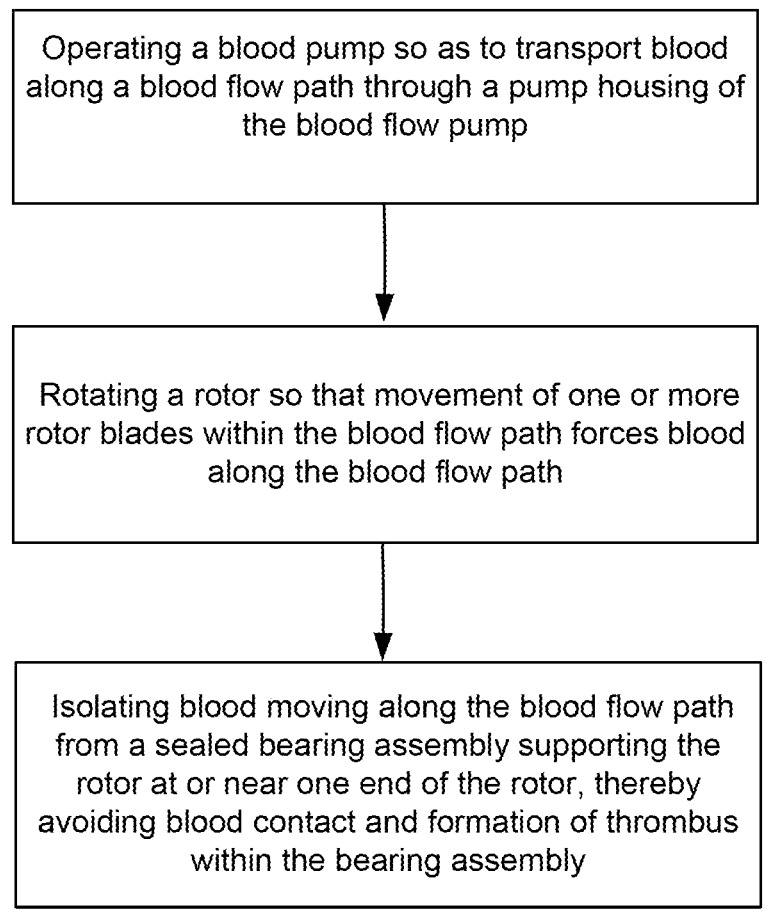

FIG. 6-7 show flowcharts of exemplary methods of pumping blood with a blood pump in accordance with embodiments of the invention. FIG. 6 depicts a method of pumping blood that includes: operating a blood pump so as to transport blood along a blood flow path defined by a housing of the blood flow pump. Operation of the pump is performed by rotating a rotor of the pump by use of a stator extending about the blood flow path so that movement of one or more rotor blades on a distal portion of the rotor forces blood along the blood flow path. The method further includes: maintaining a position and/or alignment of the rotor during rotation by rotatably securing the rotor with a sealed mechanical bearing disposed outside the blood flow path thereby inhibiting thrombus formation in the sealed mechanical bearing.

FIG. 7 depicts a method of pumping blood with a blood pump that includes: operating a blood pump so as to transport blood along a blood flow path through a pump housing of the blood flow pump. Operation of the pump can be performed by rotating a rotor of the pump so that movement of one or more rotor blades within the blood flow path forces blood along the blood flow path. The method further includes: isolating blood moving along the blood flow path from a sealed bearing assembly supporting the rotor at or near one end of the rotor, thereby avoiding blood contact and formation of thrombus within the bearing assembly. Isolating blood flow from the mechanical bearing assembly can be performed by use of a radial seal or various other sealing means as would be known to one of skill in the art.

While the above embodiments depict axial flow pump device, it is appreciated that the cantilever rotor design may be utilized in various other rotary type blood pumps in accordance with the aspects described herein. In addition, the radial seals may be applied to various other embodiments to isolate various other bearing assembly designs from the blood flow path as desired. It is further appreciated that there are any number of mechanical bearing options that can be integrated within the designs described herein. For example, some embodiments may utilize integral duplex bearings and preloaded bearings that have increased precision. There are also many different types of bearing lubrication options available as well as rotary shaft seals that may be incorporated into various embodiments.

In alternative embodiments, aspects of the invention described above may be used in centrifugal pumps. In centrifugal pumps, the rotors are shaped to accelerate the blood circumferentially and thereby cause blood to move toward the outer rim of the pump, whereas in the axial flow pumps, the rotors are more or less cylindrical with blades that are helical, causing the blood to be accelerated in the direction of the rotor's axis.

In the foregoing specification, the invention is described with reference to specific embodiments thereof, but those skilled in the art will recognize that the invention is not limited thereto. Various features and aspects of the above-described invention can be used individually or jointly. It is appreciated that any of the aspects or features of the embodiments described herein could be modified, combined or incorporated into any of the embodiments described herein, as well as in various other types and configurations of pumps. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An implantable pump comprising:
a pump housing defining a flow passage therethrough;
a cantilevered rotor having a rotatable shaft and extending at least partly within the flow passage, the rotor being configured to facilitate fluid flow through the passage upon rotation of the rotatable shaft; and
a sealed mechanical bearing assembly supportingly coupling the rotatable shaft within the pump, the mechanical bearing assembly being sealed from contact with fluid flowing through the flow passage during operation of the pump.

2. The implantable pump of claim 1, wherein the mechanical bearing assembly is disposed at or near one end of the rotor such that the rotatable shaft is cantilevered.

3. The implantable pump of claim 2, wherein the mechanical bearing assembly is disposed outside the flow path defined by the pump housing.

4. The implantable pump of claim 1, wherein the cantilevered rotor extends along a first axis and the fluid flow path directs fluid along the first axis and diverts fluid flow along a second axis transverse to the first axis.

5. The implantable pump of claim 4, wherein the first and second axis are substantially perpendicular.

6. The implantable pump of claim 1, wherein the mechanical bearing assembly includes a lubricant sealed within.

7. The implantable pump of claim 1, wherein the mechanical bearing assembly includes sealed within one or more bearing components and/or lubricants that are non-biocompatible.

8. The implantable pump of claim 1, wherein the mechanical bearing assembly is sealed without any fluid channel for flushing the mechanical bearing assembly.

9. The implantable pump of claim 1, wherein the implantable pump is a blood pump and the mechanical bearing assembly is sealed from blood flowing through the flow passage so as to inhibit thrombus formation by avoiding contact between the mechanical bearing assembly and any blood flowing through the flow passage.

* * * * *